US00PP34258P2

(12) United States Plant Patent
Kerley

(10) Patent No.: US PP34,258 P2
(45) Date of Patent: May 17, 2022

(54) ***PRIMULA* PLANT NAMED 'KERPOLSOPIN'**

(50) Latin Name: *Primula elatior*
Varietal Denomination: KERPOLSOPIN

(71) Applicant: Kerley & Co. Ltd., Cambridge (GB)

(72) Inventor: David William Kerley, Cambridge (GB)

( * ) Notice: Subject to any disclaimer, the term of this patent is extended or adjusted under 35 U.S.C. 154(b) by 0 days.

(21) Appl. No.: 17/403,358

(22) Filed: Aug. 16, 2021

(51) Int. Cl.
*A01H 5/02* (2018.01)
*A01H 6/00* (2018.01)

(52) U.S. Cl.
USPC ..... Plt./472

(58) Field of Classification Search
USPC ..... Plt./472
See application file for complete search history.

*Primary Examiner* — Susan McCormick Ewoldt
(74) *Attorney, Agent, or Firm* — Cassandra Bright

(57) ABSTRACT

A new and distinct cultivar of *Primula elatior* plant named 'KERPOLSOPIN' is disclosed, characterized by large, soft pink, double flowers borne on umbels held above the foliage. This combination is large double flowers on a polyanthus type *Primula* is a novelty. Plants are vigorous and sterile. The new variety is a *Primula elatior*, suitable for outdoor landscape and container use.

2 Drawing Sheets

Figure 1:
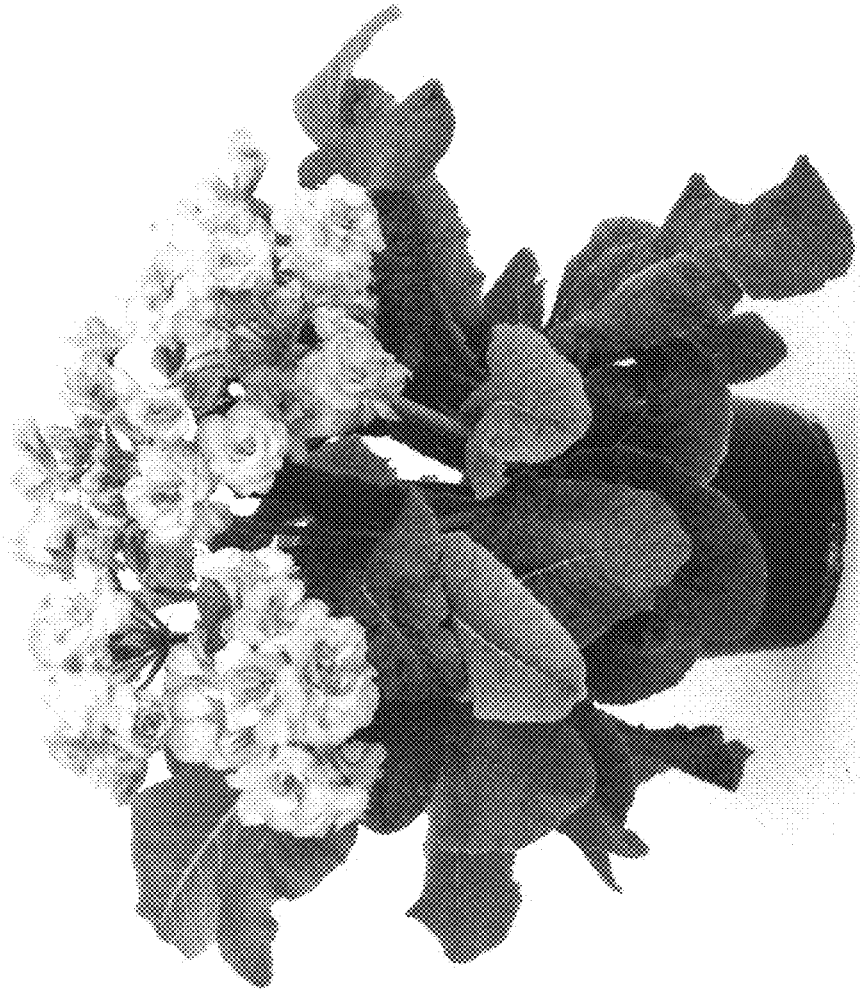

Latin name of the genus and species: *Primula elatior.*
Variety denomination: 'KERPOLSOPIN'.

BACKGROUND OF THE INVENTION

The new cultivar is the product of a planned breeding program under the direction of the inventor, David Kerley. The objective of the breeding program was to produce new *Primula elatior* cultivars with abundant double flowers for commercial ornamental purposes. The new cultivar resulted from crossing of the seed parent, an unpatented, unnamed, proprietary variety of *Primula elatior*, and the pollen parent, a different unnamed, unpatented, proprietary variety of *Primula elatior*. The crossing resulting in the new variety was made in April of 2010 at a research greenhouse in Cambridge, UK. Selection of the new variety 'Kerpolsopin' was made in March of 2011, by the inventor at a research greenhouse located in Cambridge, UK.

Asexual reproduction of the new cultivar 'KERPOLSOPIN' was first performed in Cambridge, UK during March of 2012, by tissue culture. This and subsequent propagation has shown that the unique features of this cultivar are stable and reproduced true to type in successive generations.

SUMMARY OF THE INVENTION

The cultivar 'KERPOLSOPIN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERPOLSOPIN' These characteristics in combination distinguish 'KERPOLSOPIN' as a new and distinct *Primula* cultivar:

1. Polyanthus type *Primula* with large flowers.
2. Double flowers.
3. Distinctive soft pink flowers.

4. Flowers borne above foliage on an umbel.
5. Vigorous plants.

PARENT COMPARISON

Plants of the new cultivar 'KERPOLSOPIN' are similar to plants of the seed parent, in most horticultural characteristics. However, plants of the new cultivar differ in the following:

1. New cultivar has double flowers; seed parent is single flowered.
2. New variety is sterile; seed parent is fertile.

Plants of the new cultivar 'KERPOLSOPIN' are similar to plants of the pollen parent, in most horticultural characteristics. However, plants of the new cultivar differ in the following ways:

1. New cultivar has double flowers; pollen parent is single flowered.
2. New variety is sterile; seed parent is fertile.

COMMERCIAL COMPARISON

Plants of the new variety can be compared to plants of the *Primula elatior* cultivar 'Kerpolila', co-pending application Ser. No. 17/403,377. The inventor is unaware of any other large, doubled-flowered polyanthus type *Primula* with which to compare the new variety. In side-by-side comparisons conducted in Over, Cambridge, United Kingdom, plants of the new *Primula* differed from plants of the cultivar 'Kerpolila' in the following characteristics:

1. New variety's flower color is near White N155N and Purple N75B; comparator's flower has a small amount of White N155C, main colors of Purple 77B and 77C with a margin near 77A.
2. Plants of 'Kerpolisopin' are taller than plants of 'Kerpolila'.
3. Foliage of 'Kerpolisopin' is darker green than foliage of 'Kerpolila'.

BRIEF DESCRIPTION OF THE PHOTOGRAPHS

The accompanying photograph in FIG. 1 illustrates in full color a typical plant of 'KERPOLSOPIN' grown in Over, Cambridge, United Kingdom, in a glass-covered greenhouse. This plant was about 7 months old when the photographs were taken. During the production of the plants, day temperatures ranged from 5 to 15 degrees C. and night temperatures ranged from 2 to 12 degrees C.

Figure 2:
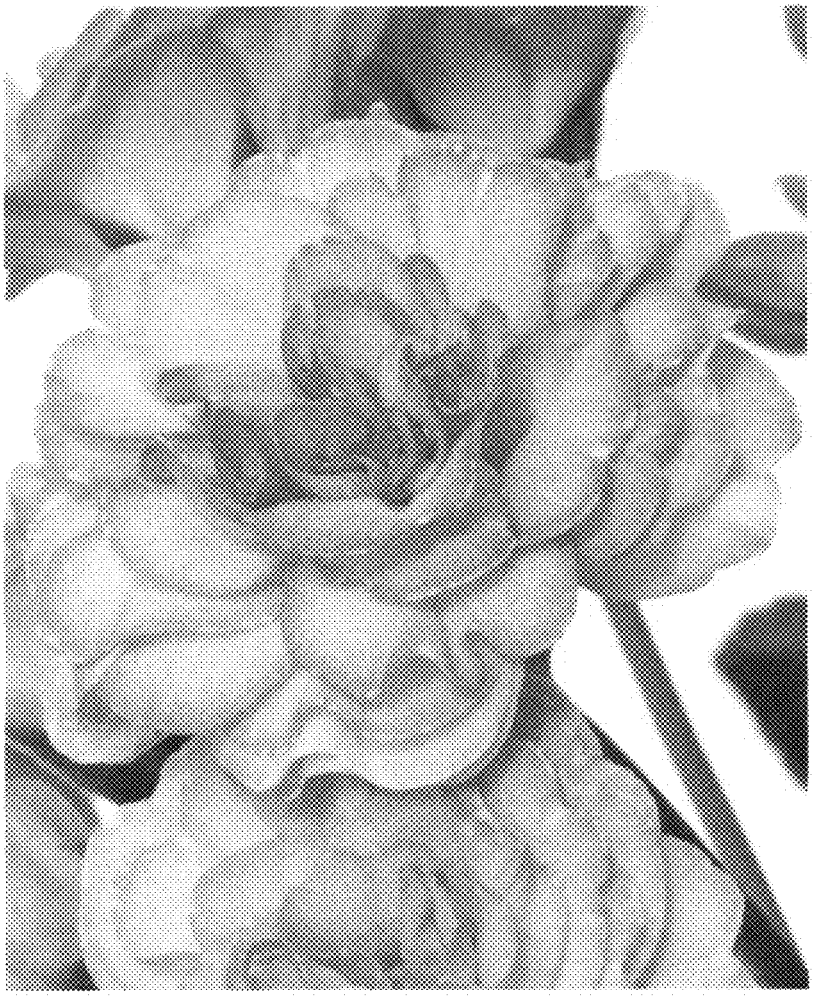

FIG. 2 illustrates a close up of a typical flower of 'KERPOLSOPIN'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 except where general terms of ordinary dictionary significance are used. The following observations and measurements describe 'KERPOLSOPIN' plants grown in a greenhouse in Cambridge, United Kingdom. During the production of the plants, day temperatures ranged from 1.5 degrees C. to 25 degrees C. and night temperatures ranged from 1.5 degrees C. to 15 degrees C. No chemical or photoperiodic treatments were given. Measurements were taken during Spring and numerical values represent averages of typical flowering types.

Botanical classification: *Primula elatior* 'KERPOLSOPIN'.

Age of the plant described: Approximately 200 days from a weaned tissue culture liner.

PROPAGATION

Method: Tissue culture.

Root description: Fibrous, colored near RHS White 155A.

PLANT

Growth habit: Upright, compact and uniform. Flowers borne on umbels above foliage.

Height: Approximately 21 cm.

Plant spread: Approximately 29 cm.

Branching characteristics: No branches, foliage emerges basally.

Vigor: Vigorous.

FOLIAGE

Leaf:

*Arrangement.*—Basal, simple.

*Average length.*—Approximately 21 cm.

*Average width.*—Approximately 8 cm.

*Shape of blade.*—Oblanceolate.

*Apex.*—Obtuse.

*Base.*—Attenuate.

*Margin.*—Crenulate, slightly undulating.

*Texture of top surface.*—Smooth, slightly rugose.

*Texture of bottom surface.*—Rugose with veins prominent.

*Color.*—Developing foliage upper side: Near RHS Yellow-Green 144A. Developing foliage under side: Near RHS Yellow-Green 144A and 144B. Mature foliage upper side: Near RHS 137A. Mature foliage under side: Near RHS Yellow-Green 144B.

*Venation.*—Type: Pinnate. Venation color upper side: Near RHS Greyed-Green overlaid with Greyed-Purple 184D near leaf base. 145C and 145D. Venation color under side: Near RHS Greyed-Green 195B.

Petiole:

*Length.*—Approximately 8 mm.

*Diameter.*—About 1 cm.

*Color.*—Upper Surface: Near RHS Greyed-Green 195B. Lower Surface: Near RHS Greyed-Green 195A and 195B.

*Texture all surfaces.*—Glabrous, smooth, slightly hirsute margins.

FLOWER

Bloom period: Recurrent flowering during the Spring under United Kingdom outdoor conditions. Very free flowering.

Inflorescence: Umbel. Average diameter range 14 to 18 cm. Average depth 5 cm.

Persistent or self-cleaning: Persistent.

Fragrance: None.

Flowers per inflorescence: 18 to 23 flowers and buds. 3 to 4 inflorescences per plant at one time.

Flower bud:

*Height.*—2.3 cm.

*Diameter.*—1.5 cm.

*Shape.*—Ovoid.

*Color.*—RHS Purple 75B.

Individual flower:

*Shape and aspect.*—Rotate, double. Upright and outwardly facing.

*Diameter.*—5 cm.

*Depth.*—3.3 cm.

*Petals.*—45 to 50 per flower, in several concentric whorls.

*Length* (*including tube*).—3.1 cm.

*Width.*—2.0 cm.

*Shape.*—Obcordate.

*Apex.*—Emarginate.

*Margin.*—Entire.

*Texture, upper and lower surfaces.*—Glabrous.

*Color.*—Developing petals, upper surface: Basal region near Yellow 12A (small region, barely visible on undissected flower), main color near White 155C with a rim of near Purple-Violet N82B. Developing petals, lower surface: Basal region near Greyed-Yellow 160B, main color near White 155C and 155D with a rim of near Purple-Violet 82C. Mature petals, upper surface: Basal region near Yellow 14A (small region, barely visible on undissected flower), main color near White N155N turning near Purple N75B towards the margin. Mature petals, lower surface: Very base of petal near Yellow 4A. Main color near White 155C and 155B becoming near Purple N75B towards the margin with a narrow rim of N75A.

*Sepals.*—Quantity per flower: 5 in a single whorl; fused at base. Length: 2.3 cm. Width: 8 mm. Shape: Lanceolate. Apex: Acute. Texture upper surfaces: Glabrous. Texture upper surfaces: Hirsute. Color, upper surface: RHS Yellow-Green 146B. Color, lower surface: RHS Yellow-Green 147B.

Peduncle:

*Peduncle length.*—15 cm.

*Peduncle diameter.*—8 mm.

*Orientation.*—Vertical, straight.

*Strength.*—Very strong.

*Color.*—Near RHS Greyed-Green 195A overlaid with Greyed-Purple 186A.
*Texture.*—Hirsute.

Pedicel:
*Pedicel length.*—5 cm.
*Peduncle diameter.*—2 mm.
*Orientation.*—Near vertical on opening flower, dropping to horizontal (90 deg to peduncle) with age in the manner of umbel flower form.
*Strength.*—Moderate.
*Color.*—Near RHS Greyed-Green 195B overlaid with Greyed-Purple 186A.
*Texture.*—Hirsute.

Bracts:
*Quantity per pedicel.*—1.
*Length.*—1.2 cm.
*Width.*—2 mm.
*Shape.*—Lanceolate.
*Apex.*—Narrowly acute.
*Texture upper surfaces.*—Glabrous.
*Texture upper surfaces.*—Hirsute.
*Color, upper surface.*—RHS Yellow-Green 144A.
*Color, lower surface.*—RHS Yellow-Green 144A.

REPRODUCTIVE ORGANS

Development of reproductive organs has not been observed.

OTHER CHARACTERISTICS

Disease resistance: Plants of the new *Primula* have not been noted to be resistant nor susceptible to pathogens and pests common to *Primula*.

Temperature tolerance: Plants of the new *Primula* have been observed to have tolerated temperatures from about −5 to 28 degrees C.

Fruit/seed production: Fruit and seed production not observed, flowers are sterile.

What is claimed is:

1. A new and distinct cultivar of *Primula* plant named 'KERPOLSOPIN' as herein illustrated and described.

* * * * *